(12) United States Patent
Priem et al.

(10) Patent No.: US 12,343,175 B2
(45) Date of Patent: Jul. 1, 2025

(54) METHOD AND SYSTEM FOR EVALUATING THE QUALITY OF A PHYSIOLOGICAL SIGNAL

(71) Applicant: BIOSENCY, Saint-Grégoire (FR)

(72) Inventors: Gurvan Priem, Rennes (FR); Quentin Bodinier, Lyons (FR)

(73) Assignee: BIOSENCY, Saint-Grégoire (FR)

( * ) Notice: Subject to any disclaimer, the term of this patent is extended or adjusted under 35 U.S.C. 154(b) by 637 days.

(21) Appl. No.: 17/763,323

(22) PCT Filed: Oct. 2, 2020

(86) PCT No.: PCT/EP2020/077728
§ 371 (c)(1),
(2) Date: Mar. 24, 2022

(87) PCT Pub. No.: WO2021/064213
PCT Pub. Date: Apr. 8, 2021

(65) Prior Publication Data
US 2022/0409144 A1  Dec. 29, 2022

(30) Foreign Application Priority Data
Oct. 2, 2019  (EP) ..................................... 19306265

(51) Int. Cl.
*A61B 5/00* (2006.01)
*A61B 5/0205* (2006.01)
(Continued)

(52) U.S. Cl.
CPC .......... *A61B 5/7221* (2013.01); *A61B 5/0205* (2013.01); *A61B 5/14551* (2013.01);
(Continued)

(58) Field of Classification Search
CPC . A61B 5/7221; A61B 5/0205; A61B 5/14551; A61B 5/681; A61B 5/721; A61B 5/7253; A61B 5/02416; A61B 2562/0219
See application file for complete search history.

(56) References Cited

U.S. PATENT DOCUMENTS 9,392,974 B2 *   7/2016  Engelbrecht ....... A61B 5/14552
2016/0360984 A1  12/2016  Albadawi et al.
2018/0325457 A1* 11/2018  Ghosh ................ A61B 5/14552

FOREIGN PATENT DOCUMENTS

CN          105550653 A      5/2016

OTHER PUBLICATIONS

International Search Report mailed Oct. 26, 2020, in corresponding to International Application No. PCT/EP2020/077728; 4 pages.
(Continued)

*Primary Examiner* — Eric F Winakur
(74) *Attorney, Agent, or Firm* — Maier & Maier, PLLC

(57) ABSTRACT

A method, intended for the evaluation of the quality of at least one periodic or quasi-periodic physiological signal, which includes the steps of: segmenting the physiological signal temporally into a plurality of signal segments; for each given signal segment, determining a distance representative of a shape difference between the given signal segment and at least one signal segment temporally offset relative to the given signal segment; and determining a quality index of the given signal segment according to the distance determined for the given signal segment.

15 Claims, 10 Drawing Sheets

(51) Int. Cl.
A61B 5/024 (2006.01)
A61B 5/1455 (2006.01)

(52) U.S. Cl.
CPC .............. *A61B 5/681* (2013.01); *A61B 5/721* (2013.01); *A61B 5/7253* (2013.01); *A61B 5/02416* (2013.01); *A61B 2562/0219* (2013.01)

(56) References Cited

OTHER PUBLICATIONS

Gartheeban Ganeshapillai; "Methods to improve the signal quality of corrupted multi-parameter physiological signals"; Massachusetts Institute of Technology; Jun. 1, 2011; XP055675006; 126 pages.

J Abdul Sukor et al., "Signal quality measures for pulse oximetry through waveform morphology analysis"; Signal quality measures for pulse oximetry; Physiological Measurement, Institute of Physics and Engineering in Medicine, Bristol; vol. 32; No. 3; Feb. 18, 2011; XP020191740; pp. 369-384.

Irene García-López et al., "Characterization Study of Neck Photoplethysmography"; 2018 40the Annual International Conference of the IEEE Engineering in Medicine and Biology Society (EMB); IEEE; Jul. 18, 2018; XP033429295; pp. 4355-4358.

Nikhilesh Pradhan et al., "Evaluation of the Signal Quality of Wrist-Based Photoplethysmography"; Dec. 1, 2017; XP055675007; 89 pages.

Jumadi Abdul Sukor; "Signal Quality Measures for Pulse Oximetry and Blood Pressure Signals Acquired in Unsupervised Home Telecare Environments"; The University of New South Wales; Nov. 26, 2012; XP055675005; 172 pages.

* cited by examiner

METHOD AND SYSTEM FOR EVALUATING THE QUALITY OF A PHYSIOLOGICAL SIGNAL

FIELD

The present invention relates to a method and a system for evaluating the quality of at least one periodic or quasi-periodic physiological signal, in particular a signal which is representative of a heart rate of a subject or modulated by a heart rate of a subject, such as a photoplethysmographic (PPG) signal, an electrocardiographic (ECG) signal, an impedance cardiography (ICG) signal, a ballistocardiographic (BCG) signal. The invention is particularly advantageous for ambulatory measurement devices, in order to discriminate between acquisitions that are exploitable and those that are to be rejected, for example due to motion artifacts, noisy environments, or unsuitable values of parameters influencing the physiological signal, such as low peripheral perfusion in the case of a PPG signal.

BACKGROUND

The invention relates to methods and systems using measurements of periodic or quasi-periodic physiological signals to determine physiological parameters of a subject, and aims more specifically to improve the reliability by selecting only high-quality portions of the physiological signals for further computation of physiological parameters of the subject. The invention is more particularly directed to physiological signals that are representative of a heart rate of a subject or modulated by a heart rate of a subject. Examples of applications include, e.g., methods and systems using PPG measurements to determine the heart rate and/or blood oxygen saturation (SpO2) of a subject; methods and systems using ECG measurements to determine the heart rate of a subject and/or heart rate variability; methods and systems using ICG measurements to determine the heart rate of a subject and/or heart rate variability; methods and systems using BCG measurements to determine the heart rate of a subject and/or heart rate variability.

As a specific example, pulse oximetry is a method for determining blood oxygen saturation (SpO2) by using specific light sources and optical sensors. Specific light wavelengths are either transmitted through or reflected from tissues of a subject and used to determine a relative proportion of oxygenated blood. The implementation of pulse oximetry aims in particular to detect cases of hypoxia, i.e. insufficient oxygenation of the cells, typically for SpO2 values below 90%. It also allows the monitoring of other clinical disorders, such as chronic obstructive pulmonary disease or asthma. Outside the medical field, pulse oximetry may also be used, e.g., for outdoor activities where the oxygen level in the air is expected to be lower than in daily life. This is the case, for example, for high-altitude sports activities, in particular those where a subject may be confronted with mountain sickness. In all of the above applications, pulse oximetry is advantageous in that it is a non-invasive, painless method that allows continuous monitoring.

In a conventional way, SpO2 measurement is performed using a pulse oximetry system comprising at least two light sources emitting at different wavelengths, for example in the red wavelength range and in the infrared wavelength range. Typically, the light sources are light-emitting diodes (LEDs) generating light signals which are acquired by an acquisition module of the pulse oximetry system after passing through tissues of the subject. For this purpose, the acquisition module is configured in a manner known per se, for example by means of a photodetector and electronic components, to record the light originating from each LED. Both the transmitted light signal and the reflected light signal fluctuate with the arterial pulse, so that the photodetector can be used in a transmission mode or a reflectance mode. The resulting signals, referred to as photoplethysmographic (PPG) signals, indicate volume changes due to blood flow. More precisely, each PPG signal exhibits a pulsing waveform, related to the heart rate of the subject, comprising successive patterns which are each representative of a heartbeat.

Measurement artifacts, including motion artifacts or other noises, can interfere with an accurate determination of SpO2. This is particularly the case for artifacts related to the activity level of the subject, which essentially result in a distortion of the waveform of the PPG signals. With the emergence of new pulse oximetry systems configured be worn daily by a subject, for example in the form of wristbands, attempts have been made to make SpO2 measurements more reliable, in particular in the presence of movements of the subject, by evaluating the quality of the patterns of a PPG signal through a quality index. The quality index is then used by the pulse oximetry system to decide, on the basis of quality criteria, whether a pattern should, or should not, be taken into account for the calculation of SpO2.

Some existing methods determine a quality index that depends on the period of the signal. Typically, this involves performing a spectral analysis of an entire PPG signal to find a main frequency component and, on the basis of this information, discriminating patterns that are, for example, not associated with a period resulting from the identified frequency. In other methods, a quality index is determined according to a shape of the signal. None of the prior art methods intended to assess the quality of a PPG signal is entirely satisfactory. In particular, the analysis of the period of a signal including artifacts, especially motion artifacts, is highly imprecise due to the fact that the variation in the signal period is sensitive to artifacts.

In addition, in the prior art methods based on the period or the amplitude of the signal, comparisons are made with predetermined values that are fixed over time, and the calculations are carried out on the basis of said fixed predetermined values. In particular, when determining a quality index based on the amplitude of a pattern, the predetermined value to which the amplitude of a pattern is compared corresponds to an individualized measurement obtained by calibrating the pulse oximetry system, or by previous measurements. Such an individualized measurement, which is related to a given environment and a given activity level of the subject, is not adjusted when the environment or activity level of the subject change. This results in a lack of adaptation of the method, thus leading to a lack of robustness and accuracy in the calculation of SpO2.

The above-mentioned drawbacks are not limited to the evaluation of SpO2. Similar problems occur when assessing the quality of other periodic or quasi-periodic physiological signals from which physiological parameters of a subject are calculated, such as ECG, ICG or BCG signals. To date, the methods available for the evaluation of the quality of physiological signals do not allow reliable and accurate determination of physiological parameters of a subject, based on physiological signals, regardless of the activity level of the subject, or without requiring calibration or individualized measurements.

It is these drawbacks that the invention is intended more particularly to remedy by proposing a method and a system for evaluating the quality of at least one periodic or quasi-periodic physiological signal, which are configured to automatically adapt to the environment and the activity level of a subject, independently from any calibration or individual measurement, so that physiological parameters of the subject can be determined with improved accuracy even with ambulatory setups. Examples of ambulatory setups include, e.g.: wrist-worn pulse oximeters; Holter monitors worn for several hours or days.

SUMMARY

For this purpose, a subject of the invention is a method for evaluating the quality of at least one periodic or quasi-periodic physiological signal, in particular a signal which is representative of a heart rate of a subject or modulated by a heart rate of a subject, said method comprising steps of:
   segmenting the physiological signal temporally into a plurality of signal segments,
   for each given signal segment, determining a distance representative of a shape difference between the given signal segment and at least one signal segment temporally offset relative to the given signal segment,
   determining a quality index of the given signal segment according to the distance determined for the given signal segment.

The method of the invention provides an evaluation of the signal quality based on a comparison of the morphology of temporally offset segments of the physiological signal. This strategy allows a continuous detection over time of changes, in the environment or the activity level of the subject, which induce modifications in the shape of the signal. Based on a continuous shape comparison over time of temporally offset segments, it is thus possible to exclude portions of the signal comprising motion artifacts or other noises and use only high-quality portions of the signal for the determination of the corresponding physiological parameters of the subject.

According to one feature of the method, for each given signal segment, the or each temporally offset signal segment to which the given signal segment is compared is comprised in a temporal window around the given signal segment, the temporal window being a different window for each given signal segment. In other words, a temporal window is associated to each given signal segment and is not the same from a given signal segment to another given signal segment. Such an evolutive temporal window associated with successive given signal segments ensures that the signal segment(s) used for the shape comparison are updated according to latest changes in the environment or in the activity level of the subject. The method of the invention thus permanently integrates changes in the environment or the activity level of the subject, which makes it more adaptive over time, thus leading to an improved robustness and accuracy in the calculation of physiological parameters of the subject.

According to one embodiment of the method, the signal segments produced in the step of segmenting the physiological signal are signal segments all having the same temporal length selected to be higher than or equal to the predefined longest period of the physiological signal. In an advantageous manner, in this embodiment, it is not required to identify successive patterns of the physiological signal, and the segmentation step is implemented simply by dividing the physiological signal into signal segments all having the same temporal length. The removal of the step of identification of successive patterns of the physiological signal is beneficial in terms of signal processing.

The predefined longest period (also called herein longest period) is a predefined value representing the longest period that a physiological signal may have in an average population of individuals and may have been clinically estimated, or obtained from literature or clinical databases. Therefore, the predefined longest period is not estimated on the signal under evaluation but is known a priori.

In a preferred embodiment, the method comprises:
   segmenting the physiological signal temporally into a plurality of signal segments, said signal segments having all the same temporal length selected to be higher than or equal to the predefined longest period of the physiological signal,
   for each given signal segment, determining a distance representative of a shape difference between the given signal segment and at least one signal segment temporally offset relative to the given signal segment,
   determining a quality index of the given signal segment according to the distance determined for the given signal segment.

According to one feature, the method comprises, for each given signal segment, the determination of the pointwise distance between the given signal segment and each signal segment in a temporal window around the given signal segment having a length between twice and ten times the length of the signal segment, preferably equal to a multiple of the predefined longest period of the physiological signal, and the computation of the minimum of the determined distances. Within the meaning of the invention, a "pointwise distance" between two segments corresponds to the distance computed between subsequent pairs of points in which each point belongs to a distinct segment, and a "temporal window around the given signal segment" may be a forward window, i.e. a time window starting at the starting point of the given signal segment; a backward window, i.e. a time window ending at the end point of the given signal segment; or a time window distributed on each side of the given signal segment. The use of a forward window is advantageous in that it is the most reactive to integrate changes in the environment or in the activity level of the subject and update data for the shape comparison in real time.

According to one feature, prior to the step of determining a distance, the physiological signal is transformed using a transformation function, e.g. the square root velocity function SRVF, so that the distance representative of a shape difference between two signal segments is given by the Euclidean distance between the transformed representations of the two signal segments. This transformation step makes it possible to use a simplified distance to compare the shapes of the signal segments. In particular, comparing two functions transformed with the SRVF under the Euclidean distance is equivalent to comparing the original functions under the Fisher-Rao metric, which is well suited for shape comparison.

According to one feature, a sliding distance matrix of the physiological signal is computed, comprising for each given signal segment a vector of the Euclidean distances between the transformed representation of the given signal segment and the transformed representation of each signal segment in a temporal window around the given signal segment having a length at least twice the length of the signal segment, preferably equal to a multiple of the predefined longest period of the physiological signal.

According to one feature, a sliding matrix profile is computed, being the series of the minimal Euclidean distances between the transformed representation of each given signal segment starting at a specific point, and the transformed representation of all the other signal segments of same temporal length in a temporal window around the given signal segment having a length at least twice the length of the signal segment, preferably equal to a multiple of the predefined longest period of the physiological signal.

Otherwise said, according to one embodiment, the method comprises:
  computing a sliding distance matrix by calculating, for the transformed representation of each given signal segment starting at a point and of duration, the distance to all signal segments starting at a point and of duration comprised in a temporal window around of length between twice and ten times the length, wherein said sliding distance matrix has cells comprising the distance between segments; and
  for each column of the sliding distance matrix, computing the minimum distance value of each column, yielding a so-called sliding matrix profile consisting of a vector of the minimal distance between the transformed representation of each given signal segment to all the transformed representation of signal segments in a temporal window around the given signal segment having a length between twice and ten times the length of the signal segment, so that the sliding matrix profile vector comprises the distance for each given signal segment.

According to one feature, the segments of the physiological signal are normalized in amplitude before the computation of the sliding distance matrix.

According to one feature, for the computation of the sliding distance matrix, for each pair of signal segments $T_{i,m}=\{t_i:t_{i+m}\}$, $T_{j,m}=\{t_j:t_{j+m}\}$ having a temporal length m, the distance between the two signal segments of the pair is computed as:

$$d_{ij} = \sqrt{2m\left(1 - \frac{C_{ij} - m^{-1}A_iA_j}{\sqrt{(B_i - m^{-1}A_i)(B_j - m^{-1}A_j)}}\right)}$$

where:

$$A_i = \sum_{k=0}^{m-1} t_{i+k}$$

$$B_i = \sum_{k=0}^{m-1} t_{i+k}^2$$

$$C_{ij} = \sum_{k=0}^{m-1} t_{i+k} t_{j+k}$$

According to one feature, the combined quality of at least a first and a second periodic or quasi-periodic physiological signals recorded simultaneously, e.g. two PPG signals associated with two different wavelengths $\lambda_1$ and $\lambda_2$, is evaluated by computing a combined sliding distance matrix through the expression:

sdm_c=sqrt(sdm$_1^2$+sdm$_2^2$), where sdm$_1$ is the sliding distance matrix of the first physiological signal and sdm$_2$ is the sliding distance matrix of the second physiological signal.

According to one feature, the quality of the physiological signal is evaluated taking into account data of a gyroscope recorded simultaneously with the physiological signal, so as to detect motion artifacts, by computing a motion-integrating combined sliding distance matrix sdm$_c$* obtained by multiplying the combined sliding distance matrix sdm_c with a power of the gyroscope sensor. In particular, the power of the gyroscope sensor is calculated through the L$^2$ norm of the gyroscope sensor, as follows:

gyro$_{mag}$=$\sqrt{\text{gyro}_x^2+\text{gyro}_y^2+\text{gyro}_z^2}$

According to one feature, the sliding matrix profile is computed from the sliding distance matrix by evaluating the minimum value of each column of the sliding distance matrix.

According to another embodiment of the method, the physiological signal comprises successive patterns and the method comprises a preliminary step of extracting the patterns from the physiological signal, each signal segment produced in the step of segmenting the physiological signal corresponding to one extracted pattern.

According to one feature, the method comprises, for at least one extracted pattern preceded by at least one other pattern in the physiological signal, successive steps of:
  determining a reference pattern based on at least one previous pattern preceding the extracted pattern,
  determining a distance representative of a shape difference between the extracted pattern and the reference pattern,
  computing a quality index of the extracted pattern according to the distance determined for the extracted pattern.

According to one feature, the determination of a reference pattern comprises the calculation of a weighted average of the previous patterns, the weighting coefficient of each previous pattern being a function of at least a first quantity depending on the distance associated to said previous pattern, in such a way that the higher the distance, the lower the first quantity. In this way, the reference pattern used for the shape comparison is updated continuously, with higher contribution of previous patterns having a morphology close to that of a pre-existing reference pattern.

According to one feature, each weighting coefficient of a previous pattern is equal to the product of the first quantity with a second quantity, the second quantity depending on a time difference between the considered previous pattern and the extracted pattern, in such a way that the higher the time difference, the lower the second quantity. In this way, temporally close previous patterns have a higher contribution in the update of the reference pattern used for the shape comparison, thus ensuring that changes in the environment or in the activity level of the subject are integrated regularly.

According to one feature, for each extracted pattern, the distance is determined by minimizing the Euclidean norm of the following expression:

$F(M_{ref})-F(M_i(h))$, or of the following expression:

$F(M_{ref}(h))-F(M_i)$, where:
  F is a transformation function, e.g. the square root velocity function SRVF,
  $M_{ref}$ and $M_i$ correspond respectively to the evolution of the reference pattern ($P_{ref}$) and the extracted pattern ($P_i$) as a function of time,
  h is a time-based unknown corresponding to a temporal deformation function, and representing the minimization parameter of said Euclidean norm.

According to one feature, the temporal deformation function h is determined according to the expression:

$h(t)=C_0+C_1\times\int_0^t e^{W(v)}dv$, where $C_0$ and $C_1$ are predetermined constants, and W is a function of the B-spline type.

According to one feature, the B-spline function W is of degree 1 with two control points.

According to one feature, the quality index of a given signal segment is a decreasing function of the distance determined for the given signal segment, e.g. q=1/(1+d) where d is the distance determined for the given signal segment and q is the quality index for the given signal segment.

Another subject of the invention is a computer program comprising instructions for the implementation of the steps of a method as described above when the program is executed by a computer.

Another subject of the invention is a non-transitory computer readable medium comprising instructions for the implementation of the steps of a method as described above when the instructions are executed by a computer.

Another subject of the invention is a system for evaluating the quality of at least one periodic or quasi-periodic physiological signal, said system comprising:
- an acquisition module configured to acquire the physiological signal,
- a processing module for evaluating the quality of the physiological signal configured to implement steps of:
  - segmenting the physiological signal temporally into a plurality of signal segments, for each given signal segment, determining a distance representative of a shape difference between the given signal segment and at least one signal segment temporally offset relative to the given signal segment,
  - determining a quality index of the given signal segment according to the distance determined for the given signal segment.

In one embodiment, the system comprises:
- an acquisition module configured to acquire the physiological signal,
- a processing module for evaluating the quality of the physiological signal configured to implement:
  - segmenting the physiological signal temporally into a plurality of signal segments ($T_{i,m}$; $P_i$), said signal segments ($T_{i,m}$) having all the same temporal length (m) selected to be higher than or equal to the longest period of the physiological signal,
  - for each given signal segment ($T_{i,m}$; $P_i$), determining a distance (d) representative of a shape difference between the given signal segment ($T_{i,m}$; $P_i$) and at least one signal segment ($T_{j,m}$; $P_{ref}$) temporally offset relative to the given signal segment,
  - determining a quality index (q) of the given signal segment ($T_{i,m}$; $P_i$) according to the distance (d) determined for the given signal segment.

Another subject of the invention is a system for performing a pulse oximetry, the system comprising:
- at least two light sources configured to emit at two distinct wavelengths $\lambda_1$ et $\lambda_2$,
- an acquisition module configured to acquire the PPG signals resulting from the illumination of tissues of a subject by means of said light sources,
- a processing module for evaluating the quality of each PPG signal configured to implement steps of:
  - segmenting each PPG signal temporally into a plurality of signal segments, for each given signal segment, determining a distance representative of a shape difference between the given signal segment and at least one signal segment temporally offset relative to the given signal segment,
  - determining a quality index of the given signal segment according to the distance determined for the given signal segment.

According to one feature, the system further comprises a gyroscope, the acquisition module being configured to acquire the data from the gyroscope, the processing module being configured to evaluate the quality of the physiological signal(s) taking into account data of the gyroscope recorded simultaneously with the physiological signal(s), so as to detect motion artifacts.

BRIEF DESCRIPTION OF THE DRAWINGS

Features and advantages of the invention will become apparent from the following description of two illustrative embodiments of a method and a system according to the invention, intended for the evaluation of the quality of at least one periodic or quasi-periodic physiological signal, this description being given merely by way of example and with reference to the appended drawings in which:

First Embodiment.

FIG. 5 is a graph showing the segmentation into successive patterns of a PPG signal corresponding to the IR channel of the wrist-worn monitoring device;

FIG. 6 is a graph showing an isolated pattern of the PPG signal of FIG. 5 before time normalization;

FIG. 7 is a graph showing the pattern of FIG. 6 resampled to normalize the time base;

FIG. 8 is a graph showing the transform of the pattern of FIG. 7 obtained using the square root velocity function SRVF;

FIG. 9 is a graph showing the time warping function that minimizes the distance between the SRVF representation of the pattern of FIG. 7 and a reference pattern;

FIG. 10 is a graph showing the effect of the warping on the SRVF representation of the pattern of FIG. 7;

FIG. 11 is a graph showing the SRVF representations of the pattern of FIG. 7 before and after warping superposed with the SRVF representation of a reference pattern;

FIG. 12 is a graph showing the pattern of FIG. 7 before and after warping superposed with the reference pattern.

Second Embodiment.

FIG. 13 is a graph showing the transform of the AC component of the PPG signal of FIG. 4 obtained using the square root velocity function SRVF;

FIG. 14 is a graph showing data of a gyroscope recorded simultaneously with the PPG signal of FIG. 4;

FIG. 15 is a graph showing, in the top part, the average of the SRVF transform of the AC components of two PPG signals recorded simultaneously, corresponding respectively to the red channel and the IR channel of the wrist-worn monitoring device, referred to as "average PPG", and, in the lower part, the matrix profile of the average PPG used for the determination of a quality index of the PPG signals;

FIG. 16 is a graph showing the average of the DC component of the IR PPG signal used for the computation of the corresponding ratio-of-ratio;

FIG. 17 is a graph showing the standard deviation of the AC component of the IR PPG signal used for the computation of the corresponding ratio-of-ratio;

FIG. 18 is a graph showing both the SpO2 computed from the ratio-of-ratio RR, and the filtered SpO2 obtained by filtering the SpO2 by means of a Kalman filter using the quality index.

DETAILED DESCRIPTION

Figure 1:
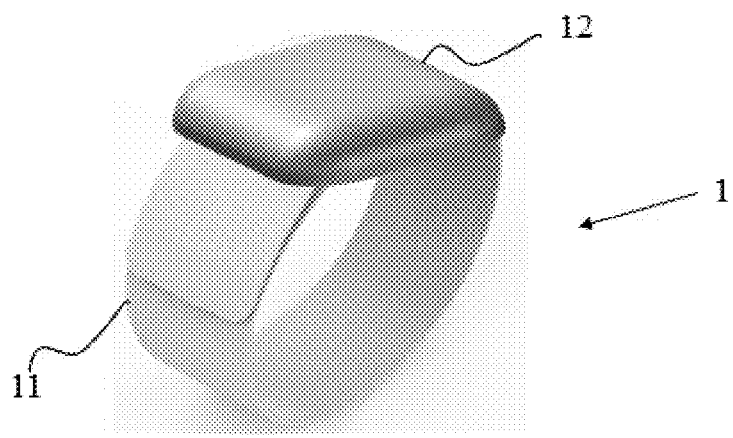
FIG. 1 is a perspective view of a wrist-worn portable monitoring device according to one embodiment of the invention.
Figure 2:
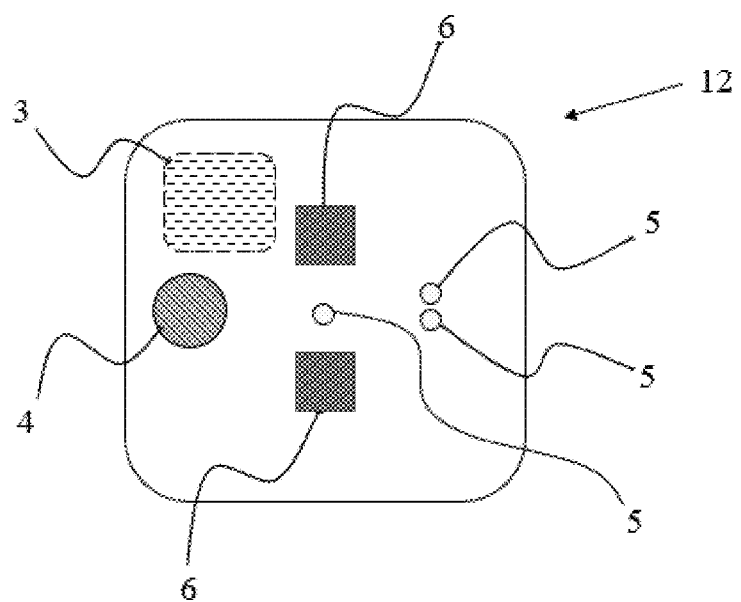
FIG. 2 is a view of the skin-side of the casing of the wrist-worn monitoring device of FIG. 1.

An example of a wrist-worn portable biometric monitoring device 1 is shown in FIGS. 1 and 2. The monitoring device 1 comprises an attachment band 11 and a casing 12 fixed to the attachment band 11. The monitoring device 1 also comprises several active elements housed inside the casing 12, i.e. a PPG sensor 2 (or photoplethysmograph), an inertial motion unit (IMU) 3 and a temperature sensor 4. The attachment band 11 is advantageously flexible and/or compliant so as to conform to the shape of a wrist of a subject. In this way, when the attachment band 11 is in place around a wrist of a subject, the casing 12 and its active elements 2, 3, 4 are close to the skin of the subject, i.e. with little to no gap between the skin-side of the casing 12 and the adjacent surface of the skin of the subject.

Figure 3:
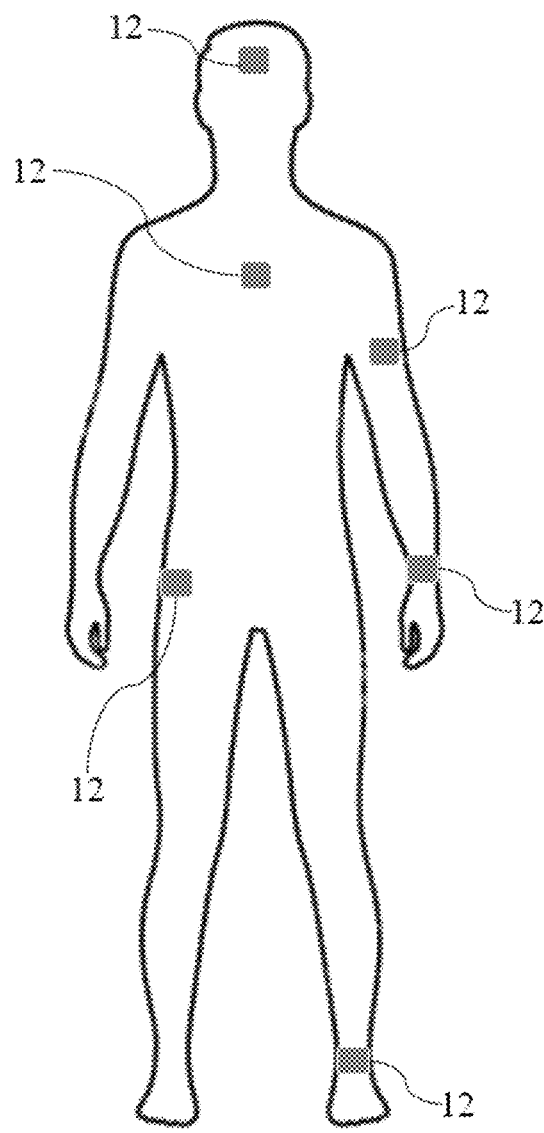
FIG. 3 is a schematic view of possible locations for a casing of a monitoring device according to the invention on the body of a subject.

The attachment band 11 may have an adjustable circumference, therefore allowing it to be closely fitted to the wrist of the subject. The attachment band 11 may be detachable from the casing 12 and, if necessary, replaceable. As illustrated in FIG. 3, the casing 12 may also be associated to attachment bands 11 of various shapes and dimensions, so that it can be worn by a subject in different locations, e.g. on the wrist, the arm, the chest, the forehead, the ankle, the leg, the hip of the subject. In FIG. 3, for clarity purposes, the various attachment bands 11 associated to the casings 12 in the different locations have not been represented.

The PPG sensor 2 of the monitoring device 1 comprises at least two light sources 5 (LED, laser, etc.) and at least one photodetector 6 (photodiode, phototransistor, etc.) arranged relative to one another so that each photodetector 6 receives the light emitted by the light sources 5 after interaction with the tissues of a subject wearing the monitoring device 1.

The light sources 5 and the photodetector(s) 6 may be placed on a flexible PCB. The monitoring device 1 also comprises a circuitry configured to determine physiological data of the subject based on the measurements of each photodetector 6, i.e. PPG signals resulting from the emission of the light sources 5, possibly combined with other measurements e.g. from the inertial motion unit 3 and the temperature sensor 4. Examples of physiological data of the subject that can be determined by means of the monitoring device 1 include the heart rate, the respiratory rate and/or the blood oxygen saturation (SpO2) of the subject.

More specifically, in the illustrative embodiment shown in FIG. 2, the PPG sensor 2 includes three light sources 5 which are three LEDs emitting light at, respectively, a red wavelength, an infrared wavelength, and a green wavelength. The PPG sensor 2 also includes two photodetectors 6 placed on both sides of the green LED, whereas the red and infrared LEDs are offset laterally relative to the interspace between the two photodetectors 6. Light pipes may be used to optically connect the LEDs 5 and the photodetectors 6 with the surface of the skin of the subject. Beneath the skin, the light from the LEDs 5 scatters off of blood in the body, some of which may be scattered or reflected back into the photodetectors 6. Due to the different positions of the three LEDs 5 in the casing 12 and the different depths of penetration of light into the tissues of the subject for the three wavelengths, different optical paths are obtained for the light of the three LEDs 5, resulting in multiple measurements by the two photodetectors 6. Such multiple measurements ensure a robust evaluation of the physiological data of the subject such as the heart rate, the respiratory rate and/or the $SpO_2$ of the subject.

In this illustrative embodiment, the inertial motion unit 3 is a 6-axis unit comprising a 3-axis gyroscope and a 3-axis accelerometer. Advantageously, the inertial motion unit 3 is entirely housed inside the casing 12, without emerging on the skin-side of the casing 12. This is represented by the dotted lines around the inertial motion unit 3 in FIG. 2, which shows the skin-side of the casing 12. The temperature sensor 4 is configured to monitor the skin temperature of the subject in the vicinity of the PPG sensor.

In prior art methods, a quality evaluation is performed by checking the consistency of computed values of the ratio-to-ratio RR with one another and with a computed heart rate. A problem of such prior art methods is that they perform poorly when the PPG channels exhibit a pulsatile signal not linked to the heart rate.

The first embodiment of the invention overcomes this problem by implementing a step of assessment of the signal quality configured to detect how successive heart beats are similar to one another. By doing so, heart beats that are corrupted, e.g. by motion artifacts or other harmful effects, are assigned a low quality index and are not considered for further RR computation.

More specifically, the method according to this first embodiment takes advantage of the following features:
- using the square root velocity function SRVF to represent the morphology of each heart beat;
- developing a low-complexity strategy to find an optimal time-warping function;
- developing a process to learn what a "clean" heart beat is in an unsupervised manner.

The successive steps of the method of the first embodiment are detailed below.

On each of the red and IR PPG channels of the wrist-worn monitoring device, the pulsatile AC signal is obtained thanks to a 4th order Butterworth band-pass filter with cutoff frequencies of 0.5 Hz and 4 Hz. The DC signal is obtained using a low-pass filter having a cutoff frequency of 0.5 Hz.

Figure 4:
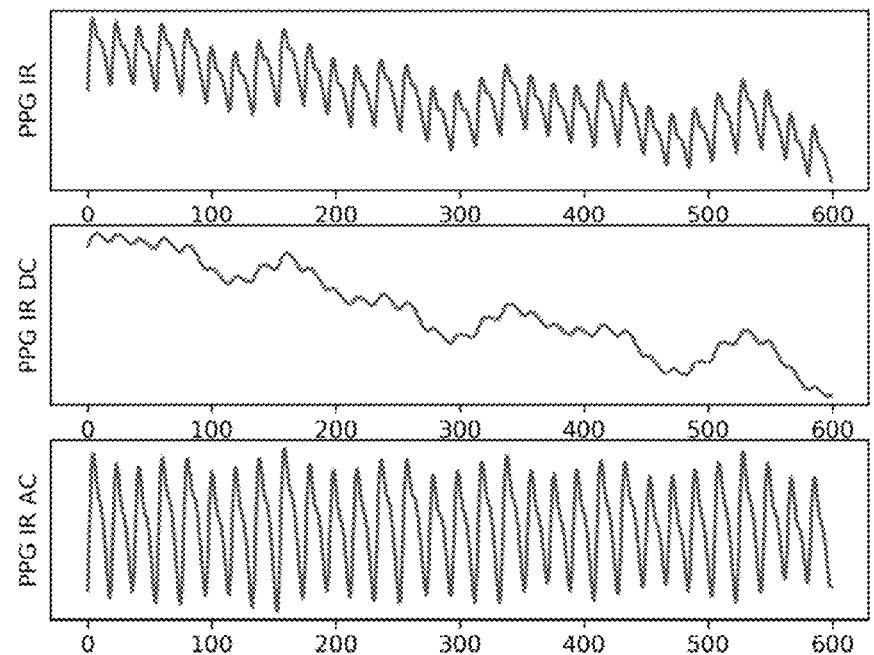
FIG. 4 is a graph showing the AC and DC components of a PPG signal corresponding to the IR channel of a wrist-worn monitoring device such as that of FIGS. 1 and 2.

By way of example, preprocessed AC and DC components of the PPG signal corresponding to the IR channel of the monitoring device are shown in FIG. 4.

In an advantageous manner, information gathered on the green PPG channel of the monitoring device is used to segment the PPG signals from the red and infrared PPG channels. More specifically, a sequence of heart beat instants $t_{b,g}[n]$ is detected on the green PPG channel and applied on the red and IR PPG channels such that:

$$\forall n,\ t_{b,r}[n]=t_{b,ir}[n]=t_{b,g}[n].$$

Then, each beat signal is constructed on the red and IR PPG channels according to the following expressions:

$$x_r[n,:]=ppg\_r[\tfrac{1}{2}(t_{b,g}[n]+t_{b,g}[n+1]):\tfrac{1}{2}(t_{b,g}[n+1]+t_{b,g}[n+2])],$$

$$x_{ir}[n,:]=ppg\_ir[\tfrac{1}{2}(t_{b,g}[n]+t_{b,g}[n+1]):\tfrac{1}{2}(t_{b,g}[n+1]+t_{b,g}[n+2])],$$

It is noted that, depending on the physical distribution of the LEDs of the monitoring device, it is possible that the green optical path differs from the red and IR optical paths. Therefore, in an improved embodiment, instead of applying directly the beat instants found on the green PPG channel to the red and IR PPG channels, each value of $t_{b,r}[n]$ and $t_{b,ir}[n]$ is determined, respectively on the red PPG channel and on the IR PPG channel, by searching the local maximum closest to the corresponding value of $t_{b,g}[n]$.

Figure 5:
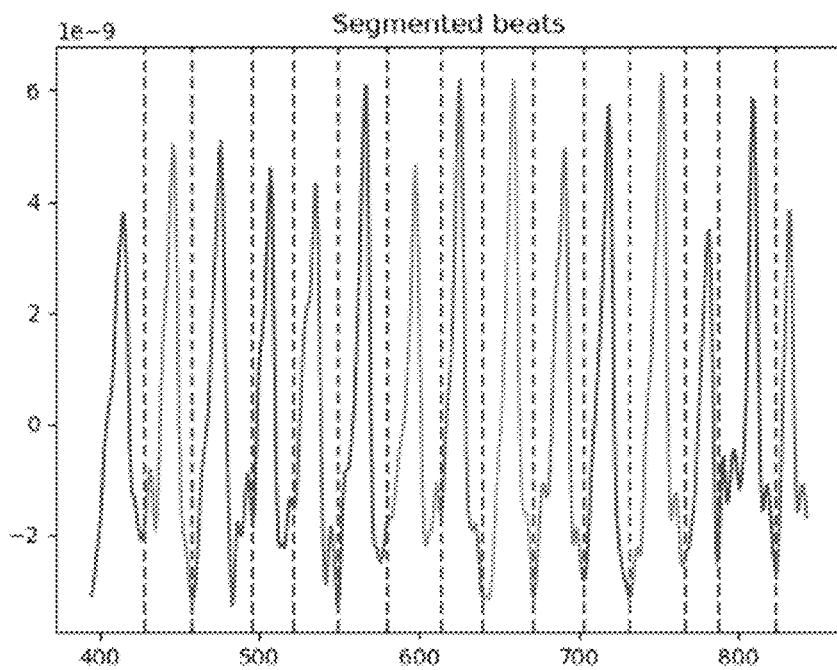
FIGS. 5 to 12

An example of the resulting segmented heart beats obtained, e.g., for the AC component of the red PPG signal of the monitoring device is shown in FIG. 5.

After the segmentation of signals from each PPG channel in successive heart beats, each heart beat is compared sequentially to a "clean" heart beat. To this end, the data are aligned using functional data analysis, and a specific distance function is used for shape comparison.

Figure 6:
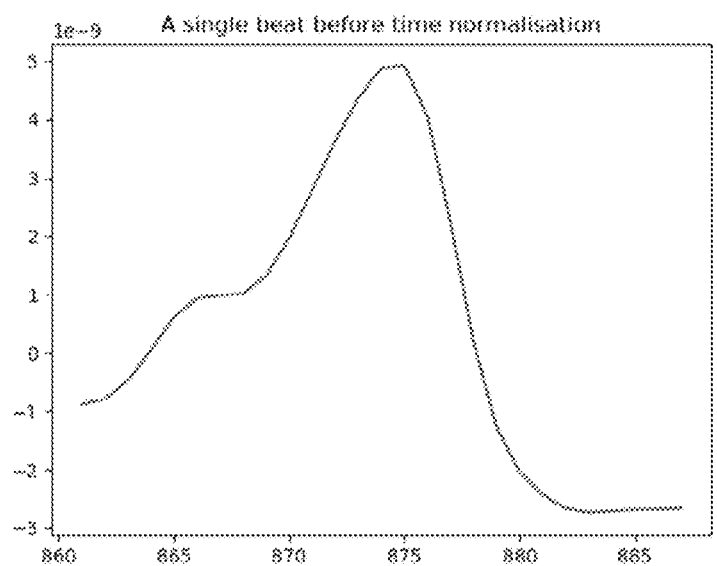
Figure 7:
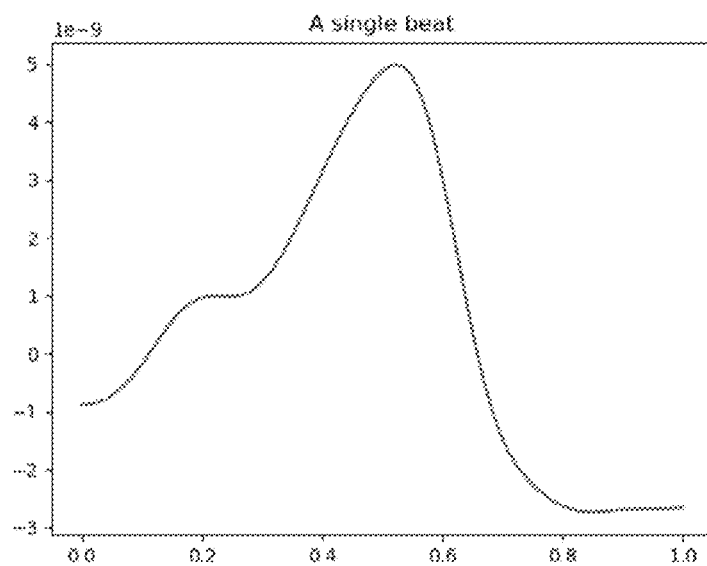
Figure 8:
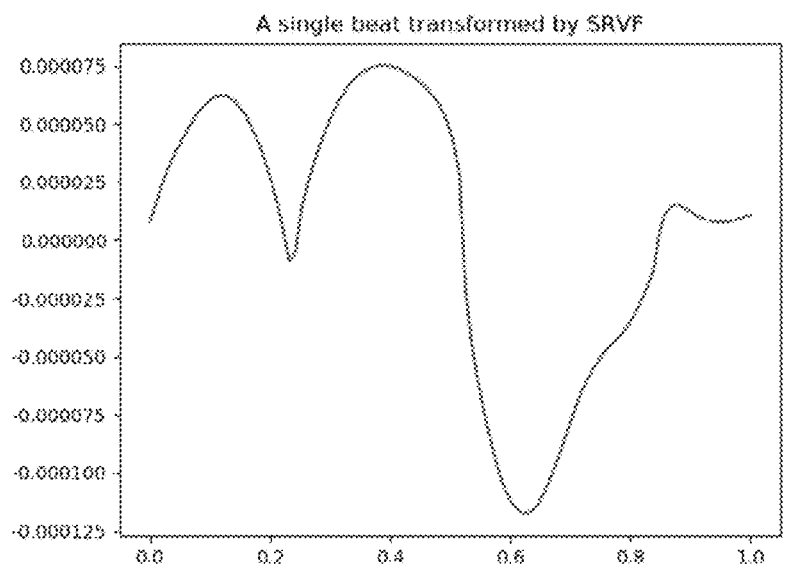

Since it is required to compare the morphology of heart beats and not specific data points, where different heart beats may have different lengths and amplitudes, the signal is preprocessed by implementing the following steps:

resampling of each heart beat to normalize the time bases. For example, for an input signal $x_0$ ranging from $t_{min}$ to $t_{max}$ and sampled at a frequency $f_s$, a resampled signal $x_1$ sampled at 100 Hz between 0 and 1 is computed. This is shown for example for the input signal $x_0$ of FIG. 6, which is converted to a resampled signal $x_1$ as shown in FIG. 7.

normalizing the minima and maxima of the resampled signal $x_1$ so that the amplitude of the signal ranges between 0 and 1. This is typically performed by computing a normalized signal $$x_2 = \frac{x_1 - \min(x_1)}{\max(x_1) - \min(x_1)}.$$

transforming the heart beats via the square root Velocity function (SRVF). The SRVF is defined as follows: $SRVF(f,x) = \text{sign}(f(x))\sqrt{|f'(x)|}$. The SRVF is particularly well suited for signal shape comparison. In an advantageous manner, comparing two functions transformed with the SRVF under the Euclidean distance is equivalent to comparing the original functions under the Fisher-Rao metric, which is more suited for shape comparison. After this step, the heart beats are represented in the SRVF space which is well suited for functional analysis. By way of example, the SRVF transform of the normalized signal corresponding to the heart beat $P_i$ of FIG. 7 is shown in FIG. 8.

Functional analysis comprises the search of a temporal deformation function h, or time warping function, that minimizes the distance between the SRVF representation of a given heart beat and the SRVF representation of a reference heart beat. In this embodiment, the temporal deformation function h is given by the following expression:

$$h: t \to C_0 + C_1 \int_0^t e^{W(v)} dv,$$

where $C_0$ and $C_1$ are predetermined constants, and W is a continuous function. In this specific embodiment, W is a B-spline function of degree 1 with two control points. More generally, the function W may be any other continuous function. B-spline functions are advantageous in that they are continuous functions that can be defined by a finite number of control points. In practice, the number of control points and the degree of the function are set, and an optimization algorithm is used to find the values of the control points.

Figure 9:
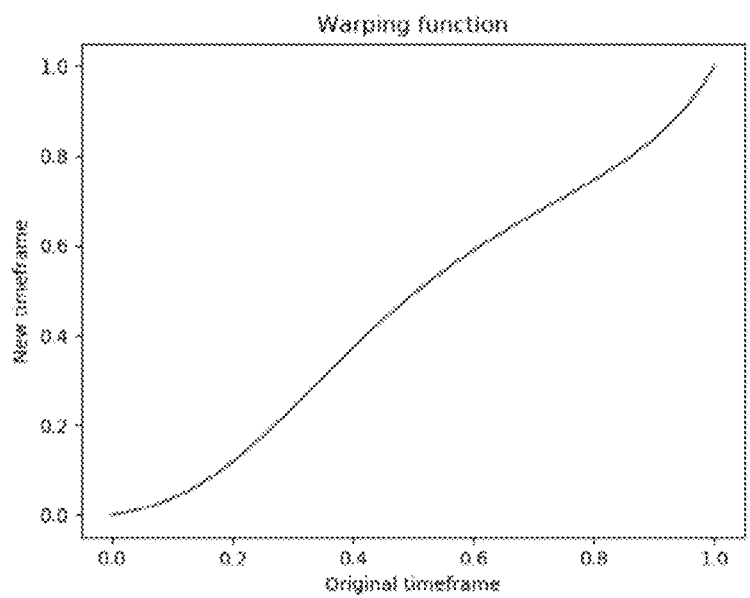
Figure 10:
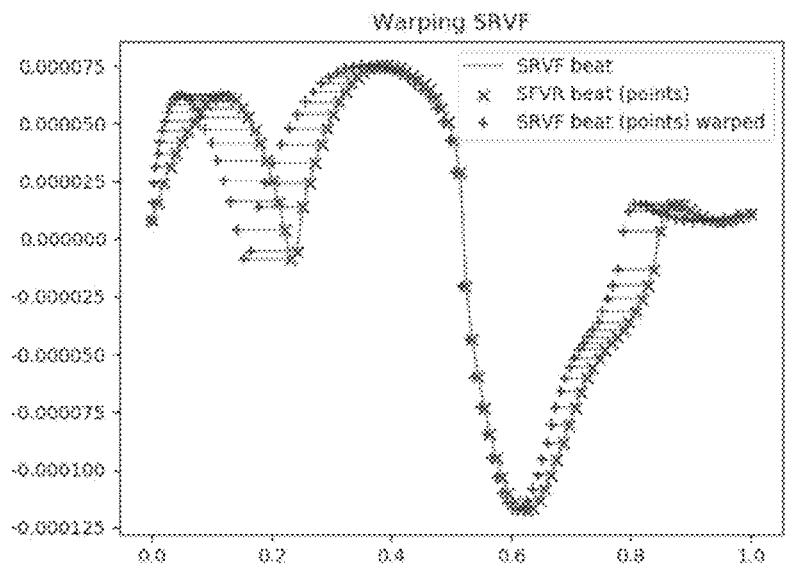

Then, functional analysis is performed to find the spline parameters which minimize the distance between the given heart beat and the reference heart beat. Since complex warping is not required in this application, a B-spline function of degree 1 with two control points, as shown in FIG. 9, is a good option for the continuous function W. FIG. 10 illustrates the deformation of the SRVF representation of FIG. 8 after warping with the temporal deformation function h.

Thereafter, the minimal distance between the given heart beat and a reference heart beat is determined for each PPG channel and is used to compute a signal quality index q of the given heart beat.

In this first embodiment, the computation of the reference heart beat is performed in an adaptive manner, by implementing the following steps:

a first heart beat is selected to initialize the reference heart beat;

for each given heart beat being processed, the SRVF representation of the given heart beat is stored and the distance between the given heart beat and the reference heart beat is computed according to the process described in the paragraph "Functional analysis" above;

after the processing of each given heart beat, the reference heart beat is updated as a weighted average of previous warped heart beats, where the weights of the previous warped heart beats are computed as the inverse of their distance to the reference heart beat multiplied by an exponential forgetting factor. For example, naming $d_b$ the distance between a previous warped heart beat and the reference heart beat, the weight of the previous warped heart beat in the computation of the new reference is computed as:

$$w_b = 1/d_b \exp(-\text{update}_{rate} * (t-t_b))$$

This process allows the reference heart beat to change slowly with the physiological parameters, thus discarding obvious artifacts. A limitation of this process is that, as long as the heart beats are similar, their quality will be considered satisfactory, even if they actually do not correspond to heart beats. For example, this may be the case in the presence of a periodic motion which may introduce periodic beats in the PPG signal that do not correspond to the pulse rate.

Therefore, in an improved variant of this embodiment, the reference signal is not initialized by a first heart beat, but by a reference control heart beat which can be obtained, e.g.:

by considering an average heart beat shape measured on several subjects, or by implementing a calibration phase in which the subject is invited to acquire a reference heart beat in optimal conditions, for example under the supervision of a health care professional.

Figure 11:
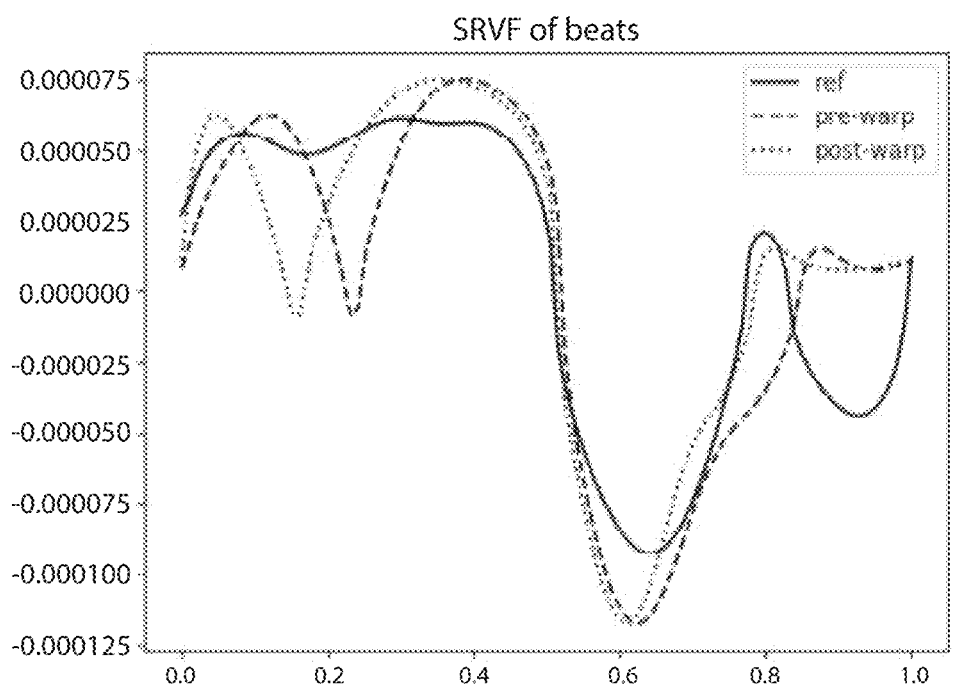
Figure 12:
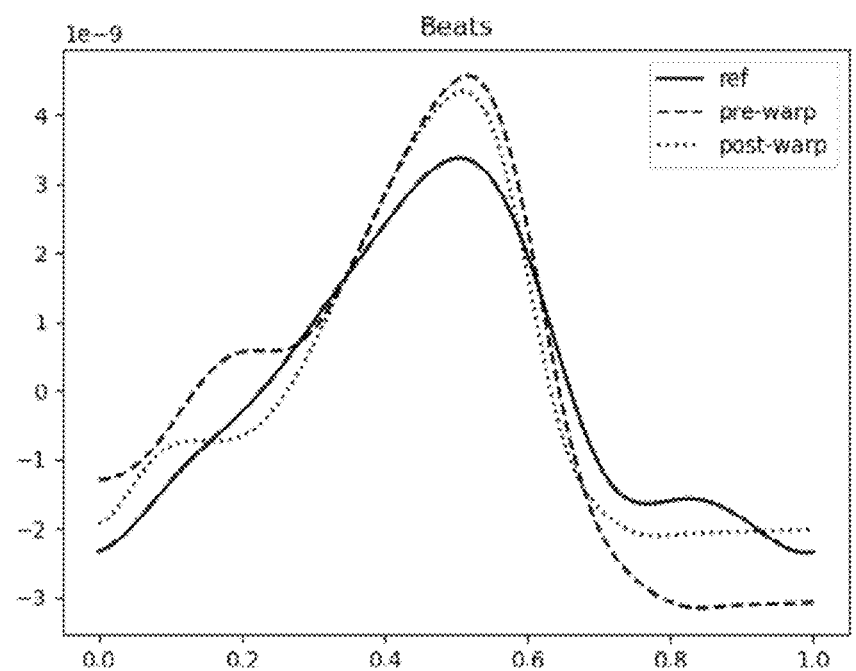

By way of example, FIG. 11 shows the SRVF representations of the heart beat $P_i$ of FIG. 7 before and after warping superposed with the SRVF representation of a reference heart beat $P_{ref}$, and FIG. 12 shows the heart beat $P_i$ of FIG. 7 before and after warping superposed with the reference heart beat $P_{ref}$.

Once the minimal distance between a given heart beat and the reference heart beat has been computed on both the red and infrared PPG channels, the distances are combined into a quality indicator for each heart beat.

Then, for a given heart beat, a quality index q is defined as:

$$q=1/((1+d_r)(1+d_{IR})).$$

This quality index may be used as an input for the assessment of the quality of the computed values of the ratio-to-ratio RR.

The ratio-to-ratio RR is determined for each heart beat by computing the following value:

$$RR[n] = \frac{std(x_r^{AC}[n,:])}{mean(x_r^{DC}[n,:])} \times \frac{mean(x_{ir}^{DC}[n,:])}{std(x_{ir}^{AC}[n,:])}$$

The outputs are the vector RR as well as the instant associated to each computed RR, depicted as $t_{RR}$.

A customized Kalman smoother making use of the quality index q computed as explained above. Apart from the observation covariance, all parameters of the Kalman smoother are set to 1. The observation covariance is set to the exponential of the squared movement adjusted quality index, $CoV_{obs}=\exp(QI_{ma}^2)$. It is noted that the exponential of the square movement adjusted quality index gives good empirical performance, but other transformation functions can also be used.

The Kalman smoother outputs both the smoothed RR signal, and the smooth state covariance, which makes it possible to compute the confidence interval of the RR value.

In the second embodiment of the invention, the step of heart beat detection is removed. Instead, signal segments are produced by dividing the signal such that each signal segment $T_{i,m}$ has a starting point i and all the signal segments have the same temporal length m, selected to be higher than or equal to the longest period of the physiological signal.

In the same way as in the first embodiment, on each of the red and IR PPG channels of the wrist-worn monitoring device, the pulsatile AC signal is obtained thanks to a 4th order Butterworth band-pass filter with cutoff frequencies of 0.5 Hz and 4 Hz. The DC signal is obtained using a low-pass filter having a cutoff frequency of 0.5 Hz.

The PPG signals from the red and IR PPG channels of the monitoring device are each divided into signal segments $T_{i,m}$ of temporal length m=2 s corresponding to 50 samples for a sampling frequency of 25 Hz. The value of the temporal length m of each signal segment $T_{i,m}$ can be reduced or increased, depending on the setup and the physiological signal to be monitored. In this embodiment, the temporal length m is about two times the temporal length of a typical pulse of the PPG signals.

This second embodiment involves, for each given signal segment $T_{i,m}$, the determination of the pointwise distance between the given signal segment $T_{i,m}$ and each signal segment $T_{j,m}$ in a forward temporal window p starting at the starting point i of the given signal segment $T_{i,m}$ and having a length n=8 s corresponding to 200 samples for a sampling frequency of 25 Hz.

Figure 13:
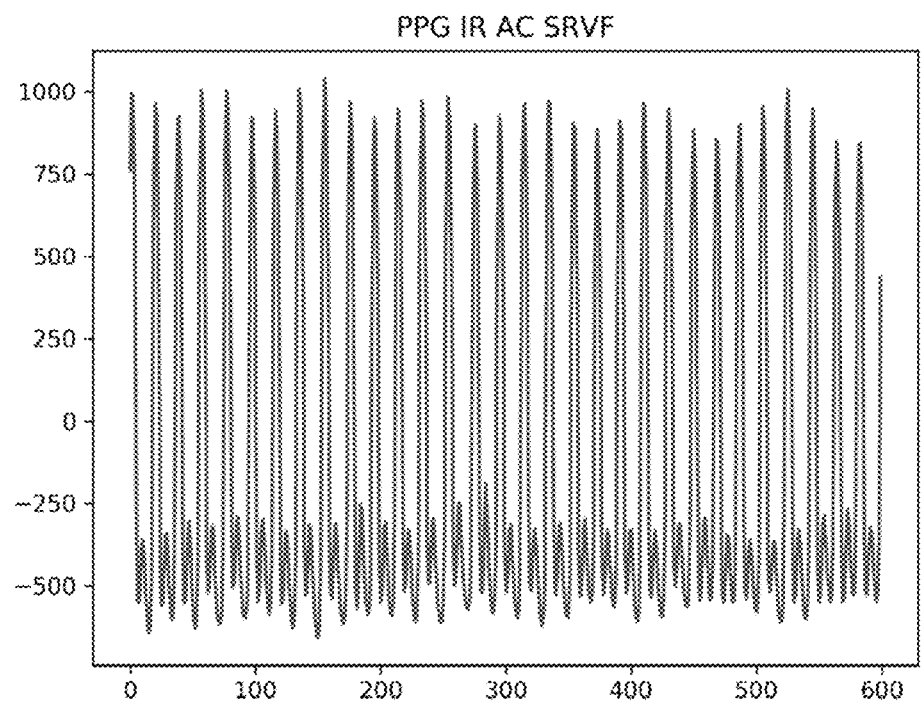
FIGS. 13 to 18

First, the AC signal on each PPG channel is transformed by applying the SRVF function so as to work in a space more suitable for morphology comparison as shown in FIG. 13. In addition, the signal segments $T_{i,m}$ are normalized in amplitude.

Then, a matrix profile algorithm is applied on the SRVF representation of the PPG AC signals. More precisely, in a first step, a sliding distance matrix is computed for the SRVF representation of each of the red and JR PPG AC signals segments starting at a point i and of duration m, the distance to all signal segments $T_{i,m}$ starting at a point j and of duration m comprised in a temporal window φ around $T_{i,m}$ of length n between twice and ten times the length m. Therefore, the sliding distance matrix comprises for each given signal segment $T_{i,m}$ a vector of the Euclidean distances between the SRVF representation of the given signal segment $T_{i,m}$ and the SRVF representation of each signal segment $T_{j,m}$ in the forward temporal window φ.

In this second embodiment, for the computation of the sliding distance matrix, for each pair of signal segments $T_{i,m}=\{t_i:t_{i+m}\}$, $T_{j,m}=\{t_j:t_{j+m}\}$ having a temporal length m, the distance between the two signal segments of the pair is computed as:

$$d_{ij} = \sqrt{2m\left(1 - \frac{C_{ij} - m^{-1}A_iA_j}{\sqrt{(B_i - m^{-1}A_i)(B_j - m^{-1}A_j)}}\right)}$$

where:

$$A_i = \sum_{k=0}^{m-1} t_{i+k}$$

$$B_i = \sum_{k=0}^{m-1} t_{i+k}^2$$

$$C_{ij} = \sum_{k=0}^{m-1} t_{i+k} t_{j+k}$$

Then, the combined quality of the red and IR PPG signals is evaluated by computing a combined sliding distance matrix sdm_c through the expression:

$$sdm\_c=\sqrt{sdm_{red}^2+sdm_{nir}^2},$$

where $sdm_{red}$ is the sliding distance matrix of the red PPG signal and $sdm_{nir}$ is the sliding distance matrix of the IR PPG signal.

The quality of the PPG signals is advantageously evaluated taking into account the gyroscope norm to detect motion artifacts. A motion-integrating combined sliding distance matrix $sdm_c^*$ is obtained by multiplying the combined sliding distance matrix sdm_c by the power of the gyroscope sensor of the inertial motion unit 3. The power of the gyroscope sensor is calculated through the $L^2$ norm of the gyroscope sensor, as follows:

$$gyro_{mag}=\sqrt{gyro_x^2+gyro_y^2+gyro_z^2}$$

Figure 15:
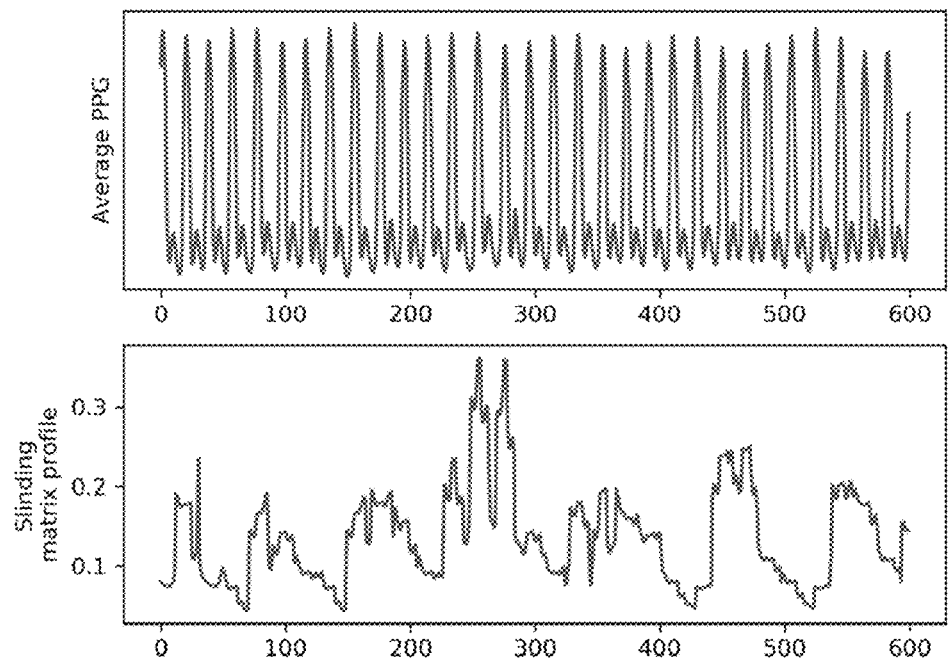

From the motion-integrating combined sliding distance matrix $sdm_c^*$, a sliding matrix profile is computed (FIG. 15), which is the series of the minimal Euclidean distances between the SRVF representation of each given signal segment $T_{i,m}$ and the SRVF representation of all the other signal segments $T_{i,m}$ of same length m in the forward temporal window p. The signal segments $T_{i,m}$ are normalized, by mean and standard deviation, before computing the Euclidean distances.

In practice, the sliding matrix profile is computed from the motion-integrating combined sliding distance matrix $sdm_c^*$ by evaluating the minimum value d of each column of the motion-integrating combined sliding distance matrix $sdm_c^*$. This gives a measure of the similarity of the given signal segment $T_{i,m}$ to its neighboring signal segments $T_{i,m}$, which is assumed to be correlated with the signal quality. Indeed, a low distance with neighbors reveals regular patterns in the data, and the distance will be increased by noise or artifacts.

This finally yields an estimation of the signal quality for each PPG signal segment $T_{i,m}$. Then, a single value of the quality index q is output every two seconds by computing the maximum on the corresponding PPG signal segment $T_{i,m}$.

The quality index q of a given signal segment $T_{i,m}$ is a decreasing function of the distance d determined for the given signal segment, e.g. q=1/(1+d).

Figure 16:
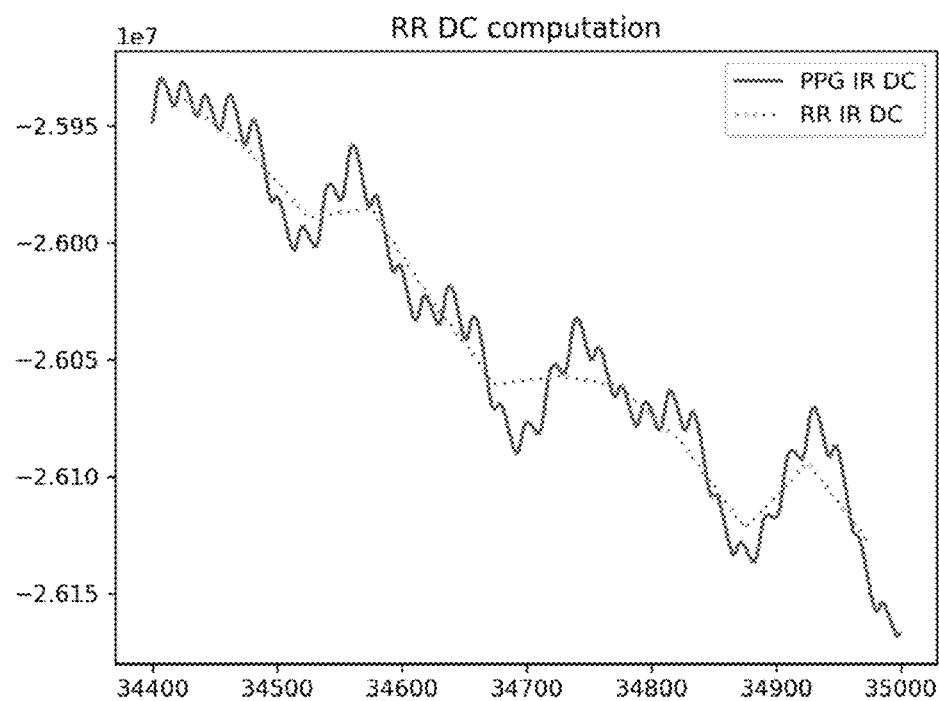
Figure 17:
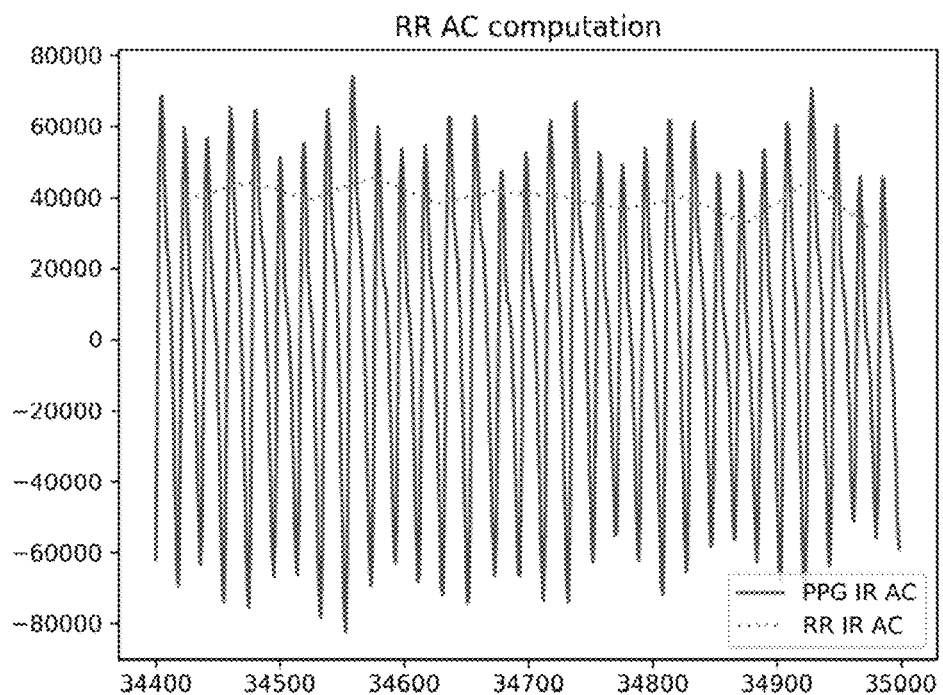
Figure 18:
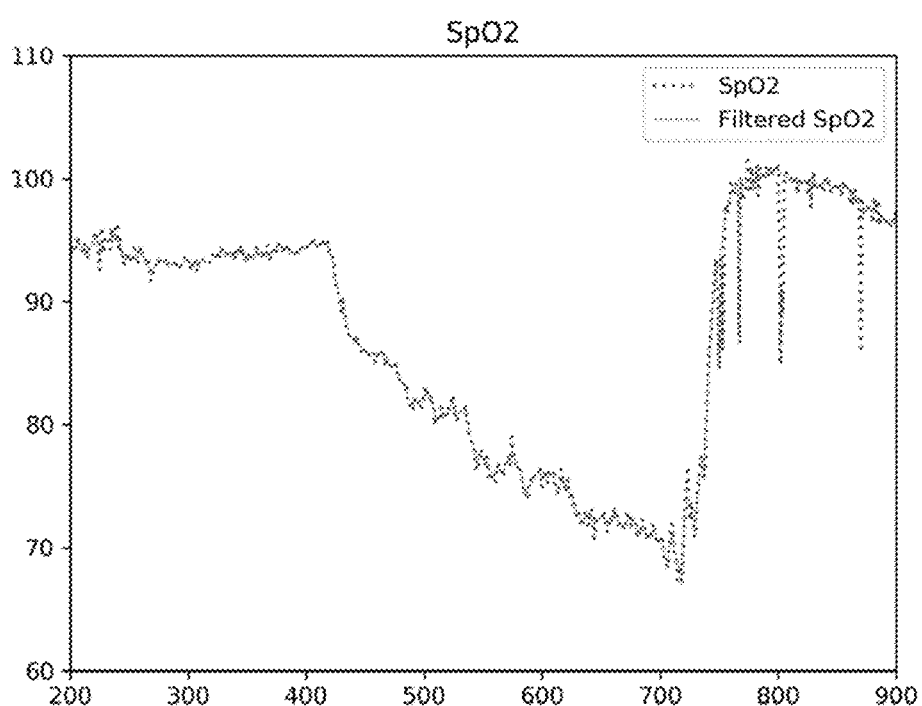

For the red and IR PPG channels of the monitoring device, for each signal segment $T_{i,m}$, the following is computed:

- on the AC components, the standard deviation of the points on the signal segment $T_{i,m}$ (FIG. 17);
- on the DC components, the average of the values observed on the signal segment $T_{i,m}$ (FIG. 16).

Then, the ratio-to-ratio RR is obtained, for each signal segment $T_{i,m}$, by computing the following value:

$$RR[i] = \frac{std(x_r^{AC}[i, m])}{mean(x_r^{DC}[i, m])} \times \frac{mean(x_{ir}^{DC}[i, m])}{std(x_{ir}^{AC}[i, m])}$$

A customized Kalman smoother is applied using the quality index q computed above.

Apart from the observation covariance, all parameters of the Kalman smoother are set to 1. The observation covariance is set to the exponential of the squared movement adjusted quality index, $Cov_{obs}=\exp(q^2)$. The exponential of the square movement adjusted quality index provides good empirical performance, but other transformation functions may be applied.

The Kalman's smoother outputs both a smoothed RR signal, and a smooth state covariance, making it possible to compute a confidence interval of the RR value.

The main cost of the algorithm of the second embodiment, both computationally and in terms of memory, comes from the distance matrix computation. However, this can be mitigated by the online nature of the algorithm. Once a specific temporal window p has been filled with a certain amount of values, the computation can be performed incrementally after each PPG signal sample is received.

For example, to compute the SpO2 on a given signal segment $T_{i,m}$ of length m and compare the signal segment $T_{i,m}$ with and each signal segment $T_{j,m}$ temporally offset relative to the given signal segment in a forward temporal window p of length n.

The normalized Euclidean distance between two signal segments $T_i=\{t_i:t_{i+m}\}$ and $T_j=\{t_j:t_{j+m}\}$ can be computed as:

$$d_{ij} = \sqrt{2m\left(1 - \frac{C_{ij} - m^{-1}A_iA_j}{\sqrt{(B_i - m^{-1}A_i)(B_j - m^{-1}A_j)}}\right)}$$

where:

$$A_i = \sum_{k=0}^{m-1} t_{i+k}$$

$$B_i = \sum_{k=0}^{m-1} t_{i+k}^2$$

$$C_{ij} = \sum_{k=0}^{m-1} t_{i+k}t_{j+k}$$

In an advantageous manner, all the values $A_i$, $B_i$ and $C_{ij}$ can be computed incrementally after each PPG sampling.

| Operation | +/− | × | ÷ | √ | Time per sample |
|---|---|---|---|---|---|
| $A_i$ | 2 | 0 | 0 | 0 | 1 |
| $B_i$ | 2 | 2 | 0 | 0 | 1 |
| $C_{ij}$ | 2 | 2 | 0 | 0 | n |
| $d_{ij}^2$ | 4 | 6 | 1 | 1 | n |
| Total | 4 + 6*n | 2 + 8*n | n | n | |

It is noted that performing a division or a square root costs about 10 times as much as an addition, subtraction or multiplication. In addition, $i \leq j < i+n$ since the distances are computed over a forward window of size n.

Since we want the minimal distance over the temporal window φ of length n, at least n comparisons per new sample are to be performed, and both the quality index q and the value of the minimum are to be stored. The memory cost is constant:

| Variable | Number |
|---|---|
| $t_i$ | m + n |
| $A_i$ | n |
| $B_i$ | n |
| $C_{ij}$ | n |
| Min index | 1 |
| Total | 4* n + m |

To compute one value of the quality index q for each SpO2 value, a maximum over n values is computed. This maximum value is stored or transmitted along with the SpO2 value. The distances have to be computed both for the red PPG signal and the IR PPG signal. They are then combined before computing the minimum over the temporal window φ.

The cost for computing the distances after each sampling can be estimated as:

$$2\times(6+14\times n+10\times 2\times n)=12+68\times n$$

For n=200, the resulting cost is around 14000 operations, which is an approximation giving an indication of the algorithm complexity. This can be performed at about 4000 times real time.

The memory requirement is about 8*n+2*m, which is 1700 floats for m=50 (=2 s) and n=200 (=8 s).

As can be seen from the previous examples, a method and a system according to the invention provide algorithmic solutions focused on signal quality assessment and RR quality assessment.

The first embodiment described above introduces an evaluation of the signal quality by comparing the morphology of each pattern of the physiological signal with a reference pattern, where the computation of the reference pattern is performed in an adaptive manner so that the reference pattern changes with the physiological parameters of the user, thus discarding obvious artifacts. Such an adaptive computation of the reference pattern can be learned in a non-supervised manner by the system.

Figure 14:
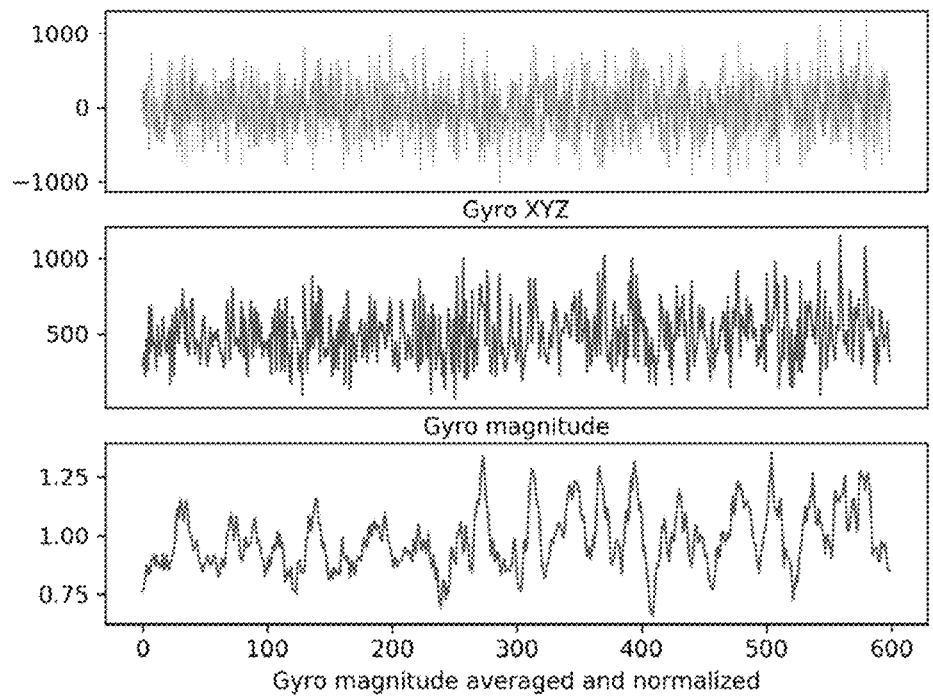

The second embodiment builds further upon this technique and simplifies it by implementing a simple pattern matching algorithm. This second embodiment has low complexity and advantageously allows for a complete removal of the step of pattern extraction, which is highly beneficial as this step is usually a burdensome procedure in signal processing. Furthermore, the second embodiment can easily be applied to multi-channel physiological sensors with more than two channels and make it possible to take into account data of a gyroscope recorded simultaneously with the physiological signal (FIG. 14).

The invention is not limited to the examples described and shown. In particular, the use of the gyroscope's power could be omitted, or replaced with the accelerometer's power, the values of m and n could be different and the Kalman smoother observation covariance expression could be modified, to $Cov_{obs}=q$ for example.

The invention claimed is:

1. A method comprising:
    segmenting a physiological signal temporally into a plurality of signal segments, each signal segment having an identical temporal length selected to be higher than or equal to a predefined longest period of the physiological signal;
    for each signal segment, continuously determining a distance representative of a shape difference between each signal segment and at least one signal segment temporally offset relative to each signal segment;
    determining a quality index of each signal segment according to the distance determined for each signal segment; and
    comparing the quality index of each signal segment to a threshold based upon quality criteria; and
    excluding each signal segment having a quality index less than the threshold.

2. The method according to claim 1, further comprising, for each given signal segment:
    determining a pointwise distance between each signal segment and each signal segment in a temporal window around each signal segment having a length between twice and ten times the length of each signal segment;
    computing a minimum of the determined distances, the pointwise distance between two signal segments corresponding to the distance computed between subsequent pairs of points in which each point belongs to a distinct signal segment.

3. The method according to claim 1, wherein, prior to determining the distance, the method further comprises:
    transforming the physiological signal using a transformation function, so that the distance representative of a shape difference between two signal segments is given by an Euclidean distance between the transformed representations of the two signal segments.

4. The method according to claim 3, wherein the transformation function is the square root velocity function.

5. The method according to claim 3, further comprising:
    computing a sliding distance matrix by calculating, for the transformed representation of each signal segment starting at a point and of duration, the distance to all signal segments starting at a point and of duration comprised in a temporal window having a length between twice and ten times the length of the signal segment, wherein said sliding distance matrix has cells comprising the distance between signal segments; and
    for each column of the sliding distance matrix, computing the minimum distance value of each column, yielding a sliding matrix profile vector of the minimal distance between the transformed representation of each signal segment to all the transformed representation of signal segments in a temporal window around each signal segment having the length between twice and ten times the length of the signal segment, so that the sliding matrix profile vector comprises the distance representative of a shape difference for each signal segment.

6. The method according to claim 5, further comprising:
    normalizing amplitudes of each signal segment of the physiological signal before the computation of the sliding distance matrix vector.

7. The method according to claim 5, wherein, for the computation of the sliding distance matrix, for each pair of signal segments $T_{i,m}=\{t_i:t_{i+m}\}$ and $T_{j,m}=\{t_j:t_{j+m}\}$ having a temporal length m, the distance between the two signal segments of the pair is computed as:

$$d_{ij} = \sqrt{2m\left(1 - \frac{C_{ij} - m^{-1}A_iA_j}{\sqrt{(B_i - m^{-1}A_i)(B_j - m^{-1}A_j)}}\right)}$$

where:

$$A_i = \sum_{k=0}^{m-1} t_{i+k}$$

$$B_i = \sum_{k=0}^{m-1} t_{i+k}^2$$

$$C_{ij} = \sum_{k=0}^{m-1} t_{i+k} t_{j+k}.$$

8. The method according to claim 5, further comprising:
    evaluating the combined quality of a first physiological signal and a second physiological signal recorded simultaneously by computing a combined sliding distance matrix through the expression:

sdm_c=sqrt(sdm$_1^2$+sdm$_2^2$), where sdm_c is the combined sliding distance matrix, sdm$_1$ is a sliding distance matrix of the first physiological signal and sdm$_2$ is a sliding distance matrix of the second physiological signal.

9. The method according to claim 5, further comprising:
    evaluating the quality of the physiological signal taking into account data of a gyroscope sensor recorded simultaneously with the physiological signal, so as to detect motion artifacts, by computing a motion-integrating combined sliding distance matrix obtained by multiplying the combined sliding distance matrix with a power of the gyroscope sensor.

10. The method according to claim 1, wherein the quality index of each signal segment is a decreasing function of the distance determined for each signal segment.

11. The method according to claim 10, wherein the quality index of each signal segment is related to the distance determined for each signal segment by the equation:
    q=1/(1+d) where a is the distance determined for each signal segment and q is the quality index for each signal segment.

12. The method according to claim 1, wherein each physiological signal is a signal which is representative of a heart rate of a subject or is modulated by the heart rate of the subject.

13. A system comprising:
    an acquisition module configured to acquire a physiological signal,
    a processing module configured to:
    segment the physiological signal temporally into a plurality of signal segments, each signal segment having an identical temporal length selected to be higher than or equal to a longest period of the physiological signal, for each signal segment, determine continuously a distance representative of a shape difference between each signal segment and at least one signal segment temporally offset relative to each signal segment, determine a quality index of each signal segment according to the distance determined for each signal segment compare the quality index of each segment to a threshold based upon quality criteria; and exclude each segment having a quality index less than the threshold.

14. The system according to claim 13, further comprising:

at least two light sources configured to emit light at two distinct wavelengths $\lambda_1$ and $\lambda_2$, and the acquisition module is further configured to:

acquire photoplethysmographic (PPG) signals resulting from the illumination of tissues of a subject by means of said light sources, and the processing module is further configured to:

segment each PPG signal temporally into a plurality of PPG signal segments, for each PPG signal segment, determine a distance representative of a shape difference between each PPG signal segment and at least one PPG signal segment temporally offset relative to each PPG signal segment, determine a quality index of each PPG signal segment according to the distance determined for each PPG signal segment.

15. The system according to claim 13, further comprising:

a gyroscope, the acquisition module being further configured to:

acquire the data from the gyroscope, the processing module being further configured to evaluate the quality of the physiological signal taking into account data of the gyroscope recorded simultaneously with the physiological signal to detect motion artifacts.

* * * * *